United States Patent [19]

Mueller

[11] 3,997,588

[45] Dec. 14, 1976

[54] 3,5-BISOXYGENATED 2-(ω-HALO-3-OXYGENATED-1-ALKENYL)-CYCLOPENTANE-1-HEPTANOIC ACIDS AND DERIVATIVES THEREOF

[75] Inventor: Richard A. Mueller, Northbrook, Ill.

[73] Assignee: G. D. Searle & Co., Chicago, Ill.

[22] Filed: May 15, 1975

[21] Appl. No.: 577,675

[52] U.S. Cl. .................. 260/468 D; 260/345.1; 260/315.7; 260/345.8; 260/410; 260/448.8 R; 260/488 R; 260/514 D

[51] Int. Cl.² ........................ C07C 177/00

[58] Field of Search .................. 260/468 D, 514 D

[56] References Cited

UNITED STATES PATENTS

| | | | |
|---|---|---|---|
| 3,833,640 | 9/1974 | Pike | 260/468 |
| 3,843,712 | 10/1974 | Axen | 260/468 |
| 3,853,951 | 12/1974 | Bernady et al. | 260/468 |

OTHER PUBLICATIONS

Yale, J. Med. Pharm. Chem., 1, 121, (1959).

*Primary Examiner*—Robert Gerstl
*Attorney, Agent, or Firm*—John A. Dhuey; Michael T. Murphy

[57] ABSTRACT

3,5-Bisoxygenated 2-(ω-halo-3-oxygenated-1-alkenyl)-cyclopentane-1-heptanoic acids and derivatives thereof, conveniently obtained by processes utilizing 2-formyl-3-hydroxy-5-oxycyclopent-1-eneheptanoic acids as the starting materials, display valuable pharmacological properties, e.g. anti-fertility, bronchodilating, anti-secretory, smooth muscle stimulatory, and blood platelet aggregation-inhibiting.

10 Claims, No Drawings

3,5-BISOXYGENATED 2-(ω-HALO-3-OXYGENATED-1-ALKENYL)-CYCLOPENTANE-1-HEPTANOIC ACIDS AND DERIVATIVES THEREOF

The present invention is concerned with cyclopentane derivatives characterized by an (ω-halo-3-oxygenated)-1-alkenyl substituent and, more particularly, with 3,5-bisoxygenated 2-(ω-halo-3-oxygenated-1-alkenyl)cyclopentane-1-heptanoic acids and derivatives thereof as represented by the following structural formula

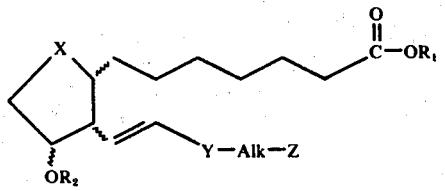

wherein $R_1$ is hydrogen or an alkyl radical containing 1–12 carbon atoms; $R_2$ is hydrogen, a tetrahydropyran-2-yl or trialkylsilyl radical, or alkanoyl radical containing 1–12 carbon atoms; X is a carbonyl or hydroxymethylene radical; Y is a carbonyl group or radical of the formula

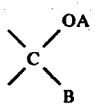

in which radical A can be hydrogen or an alkanoyl radical containing 1–12 carbon atoms and B can be hydrogen or an alkyl radical containing 1–12 carbon atoms; Z is a halo radical; Alk denotes an alkylene radical containing 3–8 carbon atoms; and the wavy lines represent the alternative α and β stereochemical configurations.

The alkyl radicals containing 1–12 carbon atoms are exemplified by methyl, ethyl, propyl, hexyl, octyl, decyl, dodecyl and the corresponding branched-chain isomers.

Representative of the alkanoyl derivatives containing 1–12 carbon atoms are formyl, acetyl, valeryl, octanoyl, nonanoyl, dodecanoyl and the branched-chain radicals isomeric therewith.

The alkylene radicals represented by Alk contain 3–8 carbon atoms and are exemplified by propylene, trimethylene, butylene, 2-methylbutylene, pentylene, hexylene and octylene.

The halo radicals denoted by Z in the foregoing structural formula are typified by chloro, bromo and iodo.

The compounds of the present invention are useful in consequence of their valuable pharmacological properties. See, for instance, Bergstrom et. al., *Pharmacol. Rev.*, 20, 1, (1968) and references cited therein. Thus, they display, for example, anti-fertility, broncho-dilating, anti-secretory and blood platelet aggregation-inhibitory activity. In addition, the present compounds are advantageous over the corresponding ω-fluro compounds which would be expected to metabolize to fluoracetate and fluoroacetic acid which are toxic substances. [See, for instance, *J. Chem. Ed.*, 50, No. 7, pp. 460–462 (1973)].

The anti-fertility properties of the instant compounds are demonstrated by their activity in the following assay:

Sexually mature female hamsters, 9–10 weeks old, are each caged with a male hamster for a period of 16–20 hours, at the end of which time vaginal smears are taken in order to determine the presence of sperm. Beginning on that day, and for four successive days thereafter, there is administered, either subcutaneously or intragastrically, to five of the inseminated females the selected dose of the test compound dissolved in a suitable vehicle, e.g. corn oil. On the sixth day the animals are sacrificed; the entire reproductive tract is then removed and the uterus and ovaries trimmed of extraneous tissue. The total number of implantation sites is counted and designated as normal or abnormal depending upon their size, color and evidence of resorption. The total number of corpora lutea also is counted and designated normal or abnormal on the basis of color and evidence of regression. Red corpora are considered normal, while pale, pink or white, regressed corpora are considered abnormal.

A single does of the test compound is classified as active if the implantation rate is 50% or less. Percent implantation is determined by the following formula:

$$\% \text{ implantation} = \frac{\text{total number of normal implantation sites}}{\text{total number of normal } corpora \; lutea} \times 100$$

The $ED_{50}$ of a compound is approximated by inspection or calculated according to the method of Berkson, *J. Amer. Stat. Assoc.*, 48 (263); 565, (1953). Estrone is employed as the standard and a relative potency is obtained from the ratio of the $ED_{50}$ of estrone to that of the test compound.

Additionally, the smooth muscle stimulating activity of the instant compounds is determined by the following assay:

Activity of the test compound on isolated segments of ascending colon from gerbils is determined using a modification of the method of Weeks, Schultz, and Brown, [*J. Appl. Physiol.*, 25, 783–5 (1968)]. The ascending colon is removed from 80–120 gram, mature, male *Meriones unguiculatus* and mounted in 2 ml. of de Jalon's solution as described by Ambache et. al. [*J. Physiol.*, London, 176, 378–408, (1965)]. The bath is maintained at 30° C., gassed with $O_2$, and suspended. Contractions are measured with a Narco Biosystems isotonic transducer and recorded on a Narco Biosystems physiograph. Two four-point parallel line bioassays are conducted on separate segments of tissue, using two concentrations of test compound and two concentrations of the standard, $PGF_2$. The bath is rinsed with a de Jalon solution after each contraction of the tissue. The test compound or standard is added to the bath at four minute intervals in a Latin square design. The amplitudes of the muscle contractions are measured on the recorder paper and used to determine the potency of the test compound relative to the standard by the method of Finney [*Statistical Method in Biological Assay*, 2nd. ed. (1964)].

Manufacture of the compounds of the present invention is conveniently achieved by processes which utilize as starting materials compounds of the following formula

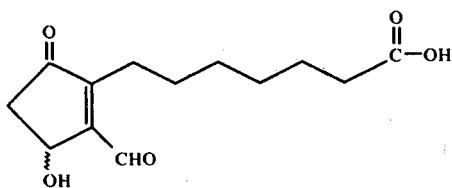

wherein the wavy line denotes the alternative α and β stereochemical configurations. Those starting materials and methods for their production are described by Miyano and Dorn, *J. Am. Chem. Soc.*, 95, 2664 (1973) and by Marsheck and Miyano, *Biochim. et Biophys. Acta*, 316, 363 (1973). The 3-hydroxy substituent is optionally protected by a suitable blocking group, e.g. tetrahydropyran-2-yl, trialkylsilyl, etc., and the resulting derivative is reduced, typically by reaction with chromous sulfate, as described by Miyano in U.S. Pat. No. 3,810,936, issued May 14, 1974, to afford the resulting intermediates of the following formula

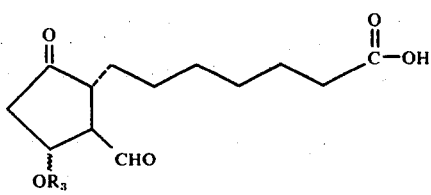

wherein $R_3$ represents the aforementioned protecting group. Reaction of those intermediates with an (ω-haloalkanoyl-methylene)tri-(substituted)phosphorane affords the instant compounds of the following formula

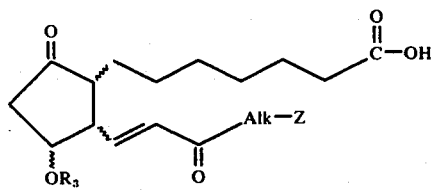

wherein $R_3$, Alk, Z, and the wavy lines have the same meaning as indicated hereinbefore.

The required (ω-haloalkanoylmethylene)tri-(substituted)phosphoranes are obtained by processes originating with hydroxyalkanoic acid lactones of the following formula

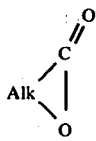

wherein Alk has the same meaning as defined hereinbefore. These lactones and methods for their preparation are described by Starcher and Phillips, [*J. Am. Chem. Soc.*, 80, 4079 (1958)] and by House, ["Modern Synthetic Reactions", p. 323, 2nd edition, W. A. Benjamin, Inc., Menlo Park, California (1972)]. These lactones are converted to the corresponding ω-haloalkanoyl halides, typically by the method described by Reppe et al., [*Ann.*, 596, 158 (1955)] for the synthesis of 4-chlorobutyryl chloride from γ-butyrolactone. Reaction of the ω-haloalkanoyl halides with diazomethane affords the corresponding diazoketones, which when treated with hydrochloric, hydrobromic or hydroiodic acid, yield the ω-haloalkylhalomethyl ketones. The latter substances are allowed to react with trisubstitued phosphines, e.g. triphenylphosphine, tri-(n-butyl)phosphine, tri-(N-dimethylaminopheny)phosphine to produce the corresponding (ω-halo-2-oxoalkyl)tri-(substituted)phosphonium chlorides, which are converted to the corresponding (ω-haloalkanoyl-methylene)tri-(substituted)phosphoranes by reaction with an alkaline metal hydroxide.

The latter reactions are exemplified by the cleavage of δ-valerolactone with zinc chloride and thionyl chloride to produce 5-chlorovaleryl chloride, reaction of that acid chloride with diazomethane, followed by treatment of the resulting diazomethyl ketone with hydrochloric acid to yield 1,6-dichloro-2-hexanone, and reaction of that ketone with triphenylphosphine to afford (6-chloro-2-oxohexyl)triphenylphosphonium chloride. This product is converted to (5-chloropentanoylmethylene)triphenyl phosphorane by reaction with aqueous sodium hydroxide. Condensation of that phosphorane with the aforementioned 3α-(tetrahydropyran-2-yloxy)-2β-formyl-5-oxocyclopentane-1α-heptanoic acid affords a mixture of stereoisomers, which are separated by chromatographic techniques to afford, as the major product, 3α-(tetrahydropyran-2-yloxy)-2β-(7-chloro-3-oxo-1-heptenyl)-5-oxocyclopentane-1α-heptanoic acid. Removal of the tetrahydropyran-2-yl group is effected by reaction with acetic acid in aqueous tetrahydrofuran, thus affording 3α-hydroxy-2β-(7-chloro-3-oxo-1-heptenyl)-5-oxocyclopentane-1α-heptanoic acid.

An alternate method for manufacture of the (ω-haloalkanoylmethylene)tri-(substituted)phosphoranes, wherein the halo substituent is other than chloro, involves heating (ω-chloroalkanoylmethylene)tri-(substituted) phosphoranes in a suitable solvent such as benzene to afford the corresponding heterocyclic phosphonium chloride, reacting that heterocyclic phosphonium salt with the appropriate alkali metal halide, e.g. sodium bromide, sodium iodide, etc., then reacting the resulting heterocyclic phosphonium halide with the corresponding hydrohalic acid, resulting in cleavage of the ring to yield the desired phosphonium salt. As a specific example, (5-chloropentanoylmethylene)-triphenylphosphorane is heated in benzene to afford [(tetrahydro-2H-pyran-2-ylidene)methyl] triphenyl phosphonium chloride which has the following structure

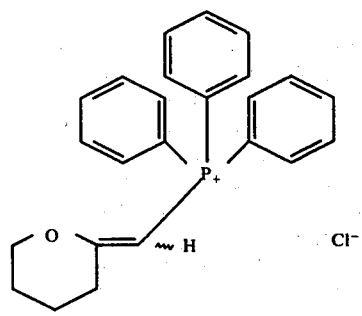

This compound is then contacted with sodium bromide to afford the corresponding phosphonium bromide, and the latter salt is heated with hydrobromic acid to yield (6-bromo-2-oxohexyl)triphenylphosphonium bromide. Reaction of that salt with aqueous sodium hydroxide affords (5-bromopentanoylmethylene)triphenylphosphorane.

These intermediate heterocyclic phosphonium salts have additional utility as anti-microbial agents. They have been found to be active in standardized tests vis a vis *Bacteroides nodosus, Fusobacterium necrophorun* and *Trichomonas vaginalis*.

Another alternate process comprises ion exchange by reaction with an appropriate ion exchange resin.

Reduction of the 3-oxo group in the alkenyl side chain of the instant compounds is achieved by the action of suitable reducing agents such as sodium borohydride, sodium cyanoborohydride, lithium tetrahydrothexyllimonyl borohydride, etc. The aforementioned 3α-hydroxy-2β-(7-chloro-3-oxo-1-heptenyl)-5-oxocyclopentane-1α-heptanoic acid, for example, is contacted with sodium cyanoborohydride to yield an isomeric mixture, which is separated chromatographically to yield 3α-hydroxy-2β-(7-chloro-3β-hydroxy-1-heptenyl)-5-oxocyclopentane-1α-heptanoic acid and 3α-hydroxy-2β-(7-chloro-3α-hydroxy-1-heptenyl)-5-oxocyclopentane-1α-heptanoic acid.

Manufacture of the instant 5-hydroxy derivatives is achieved by reduction of the corresponding 5-oxo compounds, typically by use of a reagent such as lithium perhydro-9b-boraphenalylhydride. When that reagent is contacted, for example, with 3α-hydroxy-2β-(7-chloro-3α-hydroxy-1-heptenyl)-5-oxocyclopentane-1α-heptanoic acid in tetrahydrofuran, there is produced 3α,5α-dihydroxy-2β-(7-chloro-3α-hydroxy-1-heptenyl)cyclopentane-1α-heptanoic acid. That process is further exemplified by reaction of said reagent with 3α-(tetrahydropyran-2-yloxy)-2β-(7-chloro-3-oxo-1-heptenyl)-5-oxocyclopentane-1α-heptanoic acid to effect reduction of both oxo groups. Removal of the tetrahydropyran-2-yl group is achieved by reaction with aqueous acetic acid in tetrahydrofuran to afford 3α,5α-dihydorxy-2β-(7-chloro-3αhydroxy-1-heptenyl)cyclopentane-1α-heptanoic acid and 3α,5α-dihydroxy-2β-(7-chloro-3β-hydroxy-1-heptenyl)-cyclopentane-1α-heptanoic acid.

Reaction of the 3-oxo group in the alkenyl side chain with a suitable organometallic reagent affords the corresponding (3-alkyl-3-hydroxy)-1-alkenyl derivatives. Typically, 3α-(tetrahydropyran-2-yloxy)-2β-(7-chloro-3-oxo-1-heptenyl)-5-oxocyclopentane-1α-heptanoic acid is contacted with methyl magnesium bromide; the resulting adduct is hydrolyzed with aqueous citric acid and the tetrahydropyran-2-yl group is removed in the manner previously described, i.e. by reaction with aqueous acetic acid in tetrahydrofuran, thus providing 3α-hydroxy-2β-(7-chloro-3α-hydroxy-3β-methyl-1-heptenyl)-5-oxocyclopentane-1αheptanoic acid and 3α-hydroxy-2β-(7-chloro-3βhydroxy-3α-methyl-1-heptenyl)-5-oxocyclopentane-1α-heptanoic acid.

Esterification of the instant carboxylic acids by standard techniques affords the corresponding carboxylic acid esters of the present invention. Particularly suitable reagents for this purpose are the diazoalkanes, e.g. diazomethane, diazoethane, etc. See, for example, "Organic Reactions", John Wiley and Sons, Inc., New York, N.Y., Vol. 8, pp. 389–394 (1954). Thus, 3α,5α-dihydroxy-2β-(7-chloro-3-hydroxy-1-heptenyl)cyclopentane-1α-heptanoic acid is allowed to react with an ethereal solution of diazomethane to afford methyl 3α,5α-dihydroxy-2β-(7-chloro-3-hydroxy-1-heptenyl)-5-oxocyclopentane-1α-heptanoate.

Esterification of the hydroxy compounds of the present invention, suitably by reaction with an alkanoic acid anhydride or halide, and preferably in the presence of an acid acceptor such as pyridine, triethylamine, etc., affords the alkanoyloxy compounds of the present invention. Typically, 3α-hydroxy-2β-(7-chloro-3α-hydroxy-1-heptenyl)-5-oxocyclopentane-1α-heptanoic acid is contacted, at room temperature for about 1,6 hours, with acetic anhydride and pryidine to yield 3αacetoxy-2β-(7-chloro-3β-acetoxy-1-heptenyl)-5-oxocyclopentane-1α-heptanoic acid.

The invention will appear more fully from the examples which follow. These examples are not to be construed as limiting the invention either in spirit or in scope as many modifications, both in materials and methods, will be apparent to those skilled in art. In these examples temperatures are given in degrees Centigrade (° C.) and quantities of materials in parts by weight except where otherwise noted. Nuclear magnetic resonance peaks are given in cps (cycles per second) downfield from an internal standard TMS (tetramethylsilane).

EXAMPLE 1

To an ethereal solution of diazomethane (prepared by the reaction of 90 parts of N-nitrosomethylurea with 175 parts by volume of 45% aqueous potassium hydroxide in 375 parts by volume of ether) is added dropwise, at 0° C., 50 parts of 5-chlorovaleryl chloride and the resulting reaction mixture is allowed to warm to room temperature with stirring, then stirred for an additional 16 hours. A saturated solution of dry hydrogen chloride in ether is then added portionwise to the point at which the solution becomes colorless. This solution containing the diazoketone and hydrogen chloride is stirred at room temperature for about 16 hours, then is washed successively with water, saturated aqueous sodium chloride and dried over anhydrous sodium sulfate. Removal of the solvent by distillation under reduced pressure affords 1,6-dichloro-2-hexanone.

EXAMPLE 2

To a solution of 41 parts of 1,6-dichloro-2-hexanone in 400 parts by volume of benzene is added 44 parts of triphenylphosphine and the resulting solution is stored, in the absence of light for about 6 days, at the end of which time the crude product has crystallized from the mixture. That material is collected by filtration and is purified by recrystallization from acetone to afford (6-chloro-2-oxohexyl)triphenylphosphonium chloride. This product is characterized by 60-MHz nuclear magnetic resonance peaks in $CDCl_3$(deuterated chloroform) at 100 cps (multiplet), 140 cps (multiplet), 180 cps (multiplet), 208 cps (multiplet) and 357 cps (doublet, J 12) in addition to the aromatic protons. The $C_1$ protons at 375 cps exchange with $D_2O$ (deuterated water).

EXAMPLE 3

A solution of 20 parts of (6-chloro-2-oxohexyl)-triphenylphosphonium chloride in 200 parts of water is made alkaline by the addition of a 50% aqueous sodium hydroxide solution and extracted with benzene. The combined organic extracts are dried over anhydrous sodium sulfate, then stripped of solvent under reduced pressure to afford (5-chloropentanoylmethylene)triphenylphosphorane. Alternatively, this may be used immediately as a solution in benzene.

EXAMPLE 4

A solution containing 20 parts of (5-chloropentanoylmethylene)triphenylphosphorane in 200 *parts of benzene is heated at the reflux temperature for about* 16 hours. Cooling of this solution results in crystallization of a product which is isolated by filtration to afford [(tetrahydro-2H-pyran-2-ylidene)]methyltriphenylphosphonium chloride. This product is characterized by 60-MHz nuclear magnetic resonance peaks in $CDCl_3$ (deuterated chloroform) at about 107 cps (multiplet), 170 cps (multiplet), 228 cps (multiplet) and 329 cps (doublet, J≃18 cps) in addition to the aromatic protons. This compound melts at about 215–221° C. and is represented by the following structure:

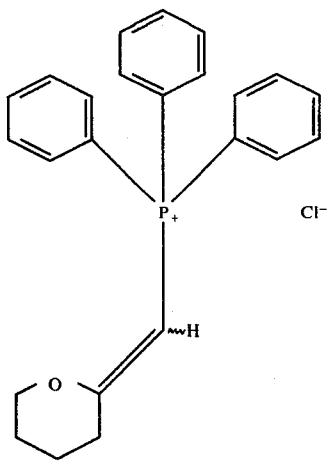

EXAMPLE 5

A solution consisting of 18.5 parts of [(tetrahydro-2H-pyran-2-ylidene)methyl]triphenylphosphonium chloride in 100 parts by volume of concentrated hydrochloric acid is heated at the reflux temperature for about 36 hours, then is cooled to room temperature. The solvent is removed by distillation under reduced pressure to afford (6-chloro-2-oxohexyl)triphenylphosphonium chloride, identical with the product of Example 2.

EXAMPLE 6

A solution consisting of 2.1 parts of [(tetrahydro-2H-pyran-2-ylidene)methyl]triphenylphosphonium chloride in 50 parts of water is added with stirring to 2 parts of sodium bromide. At the end of about 5 minutes an additional 4 parts of sodium bromide is added and the mixture is stirred until precipitation is complete. The precipitate is isolated by filtration, thus affording [(tetrahydro-2H-pyran-2-ylidene)methyl]triphenylphosphonium bromide. This product is characterized by 60-MHz nuclear magnetic resonance peaks in $CDCl_3$ (deuterated chloroform) at 107 cps (multiplet), 170 cps (multiplet), 228 cps (multiplet), 329 cps (doublet, J 18 cps) in addition to the aromatic protons, by microanalytic determination of bromide.

EXAMPLE 7

A solution consisting of 1.6 parts of [(tetrahydro-2H-pyran-2-ylidene)methyl]triphenylphosphonium bromide in 25 parts by volume of 48% hydrobromic acid is heated at the reflux temperature for about 5 hours, then is stripped of solvent under reduced pressure to afford the crude product an an amber colored oil. Trituration of that oily material with benzene, followed by evaporation of the benzene under an atmosphere of nitrogen affords (6-bromo-2-oxohexyl)triphenylphosphonium bromide. This product exhibits 60-MHz nuclear magnetic resonance peaks in $CDCl_3$ (deuterated chloroform) at about 100 cps (multiplet), 180 cps (multiplet), 200 cps (multiplet), 357 cps (doublet, J 12 cps) in addition to the aromatic protons.

EXAMPLE 8

To a solution of 39 parts of 3α-(tetrahydropyran-2-yloxy)-2β-formyl-5-oxocyclopentane-1-heptanoic acid in 100 parts by volume of tetrahydrofuran is added 44 parts by volume of (5-chloropentanoylmethylene)triphenylphosphorane and 7.8 parts of isobutyric acid. The resulting reaction mixture is stirred at room temperature for about 16 hours, at the end of which time an additional 44 parts of (5-chloropentanoylmethylene)triphenylphosphorane is added. Stirring of this mixture is continued for approximately 20 hours longer, at the end of which time the solvent is removed by distillation under reduced pressure, thus affording the crude product as a reddish-brown oil. This crude product is purified by adsorption on a silicic acid chromatographic column, followed by elution with ethyl acetate-benzene mixtures. From the 10:90 ethyl acetate-benzene eluate, there is obtained 3α-(tetrahydropyran-2-yloxy)-2β-(7-chloro-3oxo-1-heptenyl)-5-oxocyclopentane-1β-heptanoic acid. Elution of the column with a 20:80 solution of ethyl acetate-benzene affords 3α-(tetrahydropyran-2-yloxy)-2β-(7-chloro-3-oxo-1-heptenyl)-5-oxocyclopentane-1α-heptanoic acid]while the 30:70 ethyl acetate-benzene fraction affords 3α-(tetrahydropyran-2-yloxy)-2α-(7-chloro-3-oxo-1-heptenyl)-5-oxocyclopentane-1α-heptanoic acid and 3β-(tetrahydropyran-2-yloxy)-2β-(7-chloro-3-oxo-1-heptenyl)-5-oxocyclopentane-1α-heptanoic acid. Recovery of unreacted (5-chloropentanoylmethylene)triphenylphosphorane and [(tetrahydro-2H-pyran-2-ylidene)methyl]triphenylphosphonium chloride is effected by elution of the column with ethanol or an ethanol-ethyl acetate solution.

EXAMPLE 9

A solution containing 0.5 part of 3α-(tetrahydropyran-2-yloxy)-2β-(7-chloro-3-oxo-1-heptenyl)-5-oxocyclopentane-1α-heptanoic acid in 10 parts by volume of a 20:10:3 solution of acetic acid:water:tetrahydrofuran is stirred at room temperature for about 24 hours, then is diluted with distilled water and 0.1 part of 10% hydrochloric acid is added. The resulting cloudy mixture is extracted several times with ether and the ether extracts are combined, then washed successively with water, saturated aqueous sodium chloride and dried over anhydrous sodium sulfate. The solvent is removed under an atmosphere of nitrogen and the resulting crude product is purified by adsorption on a silicic acid chromatographic column followed by elution with 20% ethyl acetate in benzene, thus affording 3α-hydroxy-2β(7-chloro-3-oxo-1-heptenyl)-5-oxocyclopentane- 1α-heptanoic acid, characterized by 100-MHz nuclear magnetic resonance peaks in CD₃OD (deuterated methanol) at about 360 cps (triplet), 422 cps (broad quartet), 626 cps (doublet) and 695 cps.

When an equivalent quantity of 3β-(tetrahydropyran-2-yloxy)-2β-(7-chloro-3-oxo-1-heptenyl)-5-oxocyclopentane-1α-heptanoic acid is substituted for the 3α-tetrahydropyran-2-yloxy)-2β-(7-chloro-3-oxo-1-heptenyl)-5-oxocyclopentane-1α-heptanoic acid used above and the procedure repeated, there is obtained 7-[3β-hydroxy-2β-(7-chloro-3-oxo-1-heptenyl)-5-oxocyclopentane]-1α-heptanoic acid.

EXAMPLE 10

To a solution of 0.1 part of 3α-hydroxy-2α-(7-chloro-3-oxo-1-heptenyl)-5-oxocyclopentane-1α-heptanoic acid in 20 parts by volume of a 40:60 trifluoroethanol-methanol solution is added 0.2 part of sodium cyanoborohydride. The resulting reaction mixture is stirred at room temperature for about 6 hours, at the end of which time the reaction mixture is added to a solution consisting of 5 parts by volume of 10% hydrochloric acid, 5 parts by volume of saturated aqueous sodium chloride, and 10 parts of water. That mixture is extracted with ethyl acetate and the organic layer is separated, washed with saturated aqueous sodium chloride, then dried over anhydrous sodium sulfate. Removal of the solvent by distillation under reduced pressure affords the crude product, which is purified by adsorption on a silicic acid chromatographic column, followed by elution with a 40:60 ethyl acetate-benzene solution to afford 3α-hydroxy-2β-(7-chloro-3β-hydroxy-1-heptenyl)-5-oxocyclopentane-1α-heptanoic acid and 3α-hydroxy-2β-(7-chloro-3α-hydroxy-1-heptenyl)-5-oxocyclopentane-1α-heptanoic acid, respectively.

When an equivalent quantity of 3β-hydroxy-2β-(7-chloro-3-oxo-1-heptenyl)-5-oxocyclopentane-1α-heptanoic acid is substituted for the 3α-hydroxy-2β-(7-chloro-3-oxo-1-heptenyl-5-oxocyclopentane-1α-heptanoic acid used above and the procedure repeated, there is obtained 3β-hydroxy-2β-(7-chloro-3β-hydroxy-1-heptenyl)-5-oxocyclopentane-1α-heptanoic acid and 3β-hydroxy-2β-(7-chloro-3α-hydroxy-1-heptenyl)-5-oxocyclopentane-1αheptanoic acid.

EXAMPLE 11

To a solution of 0.09 part of 3α-hydroxy-2β-(7-chloro-3α-hydroxy-1-heptenyl)-5-oxocyclopentane-1α-heptanoic acid in 25 parts of volume of tetrahydrofuran is added, at approximately −70° C. in an atmosphere of nitrogen, 3.2 parts by volume of a 0.9 N lithium perhydro-9b-boraphenalylhydride in tetrahydrofuran solution and the reaction mixture is stirred for approximately 15 minutes after completion of the addition. The mixture is diluted with about 20 parts of water and the solution is allowed to warm to room temperature, then is diluted with an additional 60 parts of water and extracted several times with ether. The aqueous layer is separated and acidified by the addition of 1 N aqueous citric acid, then is extracted several times with ethyl acetate. The ethyl acetate extract is combined, washed with saturated aqueous sodium chloride and dried over anhydrous sodium sulfate. Removal of the solvent by distillation under reduced pressure affords the crude product as a semi-crystalline mass. Recrystallization of that crude product from ethyl acetate-cyclohexane affords 3α,5α-dihydroxy-2β-(7-chloro-3α-hydroxy-1-heptenyl)cyclopentane-1α-heptanoic acid, melting at about 90–93° C. and represented by the following structural formula

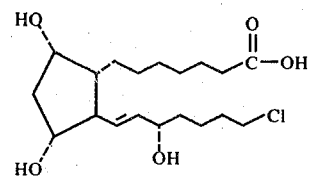

EXAMPLE 12

To a solution of 0.1 part of 3α-hydroxy-2β-(7-chloro-3α-hydroxy-1-heptenyl)-5-oxocyclopentane-1α-heptanoic acid in absolute ethanol cooled to 0° C., is added 0.07 part of sodium borohydride. The solution is stirred at 0° C. for 1 ½hours, and then 50 parts by volume of a 1 N aqueous citric acid solution is added. The resulting solution is extracted with four 20 ml. portions of ethyl acetate. The ethyl acetate fractions are combined, extracted twice with water, twice with a saturated sodium chloride solution and dried over sodium sulfate. The solvent was removed by vacuum evaporation and the resulting oil chromatographed on 10 parts of silicic acid. Elution is accomplished with increasing proportions of ethyl acetate in benzene. The 85:15 fraction of ethyl acetate-benzene affords 3α,5β-dihydroxy-2β-(7-chloro-3αhydroxy-1-heptenyl)cyclopentane-1α-heptanoic acid, while the 95:5 ethyl acetate-benzene fraction affords 3α, 5α-dihydroxy-2β-(7-chloro-3α-hydroxy-1-heptenyl)cyclopentane-1α-heptanoic acid.

EXAMPLE 13

To a solution of 2.17 parts of 3α-(tetrahydropryan-2-yloxy)-2β-(7-chloro-3-oxo-1-heptenyl)-5-oxocyclopentane-1α-heptanoic acid in 500 parts by volume of tetrahydrofuran is added, at about −78° C. in a nitrogen atmosphere, 65 parts by volume of a 0.9 N lithium perhydro-9b-boraphenalylhydride solution in tetrahydrofuran. The addition is carried out over a period of about 90 minutes. When the addition is complete, the mixture is diluted with approximately 50 parts of water, then is allowed to warm to room temperature and is diluted again with an additional 1000 parts of water. The resulting aqueous mixture is extracted several times with ether and the aqueous and organic phases are separated. The aqueous layer is acidified by the addition of aqueous citric acid, then is extracted with ethyl acetate. The ethyl acetate extracts are combined with the ether extracts, then are extracted with 5% aqueous sodium bicarbonate. The aqueous layer is separated, acidified to pH 2.5 by the addition of dilute hyrochloric acid and extracted with ethyl acetate. The combined organic extracts are washed with saturated aqueous sodium chloride and dried over anhydrous sodium sulfate, then stripped of solvent by distillation under reduced pressure to afford, as an oil, 3α-(tetrahydropyran-2-yloxy)-2β-(7-chloro-3-hydroxy-1-heptenyl)-5α-hydroxycyclopentane-1α-heptanoic acid.

The latter oily product is dissolved in 40 parts by volume of a 20:10:3 solution of acetic acid:water:tetrahydrofuran and the resulting solution is stirred at room temperature for about 24 hours, then is diluted with approximately 1200 parts of water. That aqueous mixture is extracted with ethyl acetate and the ethyl acetate layer is separated, washed with saturated aqueous sodium chloride and dried over anhydrous sodium sulfate. Evaporation of the solvent by distillation under reduced pressure affords a yellow oil, which is then adsorbed on a silicic acid chromatographic column. The column is eluted successively with ethyl acetate-hexane mixtures, ethyl acetate and acetone-ethyl acetate mixtures. From the 90:10 ethyl acetate-hexane eluate and the early 100% ethyl acetate eluate, there is obtained 3α,5α-dihydroxy-2β-(7-chloro-3β-hydroxy-1-heptenyl)cyclopentane-1α-heptanoic acid, characterized by 100-MHz nuclear magnetic resonance spectra in $CD_3OD$ with peaks at 230 cps (broad triplet), 358 cps (triplet), 409 cps (complex multiplet) and 555 cps (complex multiplet.) From the later 100% ethyl acetate eluate and the 2:98 acetone-ethyl acetate eluate, there is obtained 3α,5α-dihydroxy-2β-(7-chloro-3α-hydroxy-1-heptenyl)cyclopentane-1α-heptanoic acid melting at about 90–93° C.

EXAMPLE 14

To a solution of 0.2 part of 3α-(tetrahydropyran-2-yloxy)-2β-(7-chloro-3-oxo-1-heptenyl)-5-oxocyclopentane-1α-heptanoic acid in 20 parts by volume of tetrahydrofuran is added, at about −70° C. under an atmosphere of nitrogen, 4 parts by volume of 3.1 N ethereal methyl magnesium bromide. The resulting reaction mixture is stirred for about 1 hour, then is decanted into approximately 100 parts by volume of a mixture of ice and 1 N aqueous citric acid. Stirring is continued until the mixture warms to room temperature, at which time the solution is extracted several times with ethyl acetate. The extracts are combined, washed with saturated aqueous sodium chloride and dried over anhydrous sodium sulfate. Removal of the solvent by distillation under reduced pressure affords 3α-(tetrahydropyran-2-yloxy)-2β-(7-chloro-3-hydroxy-3-methyl-1-heptenyl)-5-oxocyclopentane-1α-heptanoic acid. The latter oily product is dissolved in 10 parts by volume of a 20:10:3 solution of acetic acid:water:tetrahydrofuran and the solution stirred at room temperature for about 16 hours. It is diluted with approximately 150 parts of water containing about 0.2 part by volume of 10% hydrochloric acid, then extracted with ethyl acetate. The extracts are combined, washed with saturated aqueous sodium chloride and dried over anhydrous sodium sulfate. Removal of the solvent by distillation under reduced pressure affords 3α-hydroxy-2β-(7-chloro-3-hydroxy-3-methyl-1-heptenyl)-5-oxocyclopentane-1α-heptanoic acid represented by the structural formula

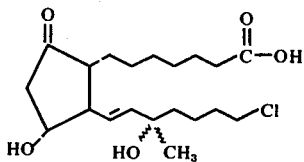

The individual isomers, 3α-hydroxy-2β-(7-chloro-3α-hydroxy-3β-methyl-1-heptenyl)-5-oxocyclopentane-1α-heptanoic acid and 3α-hydroxy-2β-(7-chloro-3β-hydroxy-3α-methyl-1-heptenyl)-5-oxocyclopentane-1α-heptanoic acid are obtained by adsorption on a silicic acid column followed by elution with a 40:60 solution of ethyl acetate-benzene.

EXAMPLE 15

A mixture consisting of 14.7 parts of 3-methyl-valerolactone and 0.15 part of freshly fused zinc chloride is stirred under a nitrogen atmosphere for about 1 hour, at the end of which time 100 parts by volume of thionyl chloride is added dropwise. At the end of the addition, the reaction mixture is heated at approximately 64° C. for about 18 hours, then is distilled to remove unreacted thionyl chloride. The resulting residue is fractionally distilled to afford 5-chloro-3-methyl-valeryl chloride, boiling at about 82–90° C. at 0.5–1mm. pressure.

EXAMPLE 16

When an equivalent quantity of 5-chloro-3-methyl-valeryl chloride is subjected to the successive processes described in Examples 1, 2, 3 and 8, there is produced 3α-tetrahydropyran-2-yloxy)-2-yloxy)-2β-(7-chloro-5-methyl-3-oxo-1-heptenyl)-5-oxocyclopentane-1α-heptanoic acid.

EXAMPLE 17

The substitution of an equivalent quantity of 3α-tetrahydropyran-2-yloxy)-2β-(7-chloro-5-methyl-3-oxo-1-heptenyl)-5-oxocyclopentane-1α-heptanoic acid in the procedure of Example 9 results in 3α-hydroxy-2β-(7-chloro-5-methyl-3-oxo-1-heptenyl)-5-oxocyclopentane-1α-heptanoic acid.

EXAMPLE 18

When an equivalent quantity of 3α-hydroxy-2β-(7-chloro-5-methyl-3-oxo-1-heptenyl)-5-oxocyclopentane-1α-heptanoic acid is substituted in the procedure of Example 10, there is produced 3α-hydroxy-2β-(7-chloro-5-methyl-3-hydroxy-1-heptenyl)-5-oxocyclopentane-1α-heptanoic acid represented by the following structural formula

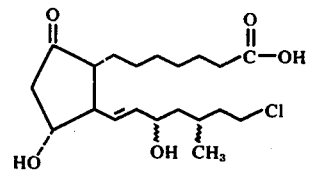

EXAMPLE 19

The substitution of an equivalent quantity of 3α-hydroxy-2β-(7-chloro-5-methyl-3-hydroxy-1-heptenyl)-5-oxocyclopentane-1α-heptanoic acid in the procedure of Example 11 results in 3α,5α-dihydroxy-2β-(7-chloro-5-methyl-3-hydroxy-1-heptenyl)cyclopentane-1α-heptanoic acid.

EXAMPLE 20

When an equivalent quantity of 3α-(tetrahydropyran-2-yloxy)-2β-(7-chloro-5-methyl-3-oxo-1-heptenyl)-5-oxocyclopentane-1α-heptanoic acid is substituted in the procedure of Example 14, there is produced 3α-hydroxy-2β-(7-chloro-3-hydroxy-3,5-dimethyl-1-heptenyl)-5-oxocyclopentane-1α-heptanoic acid.

EXAMPLE 21

The substitution of an equivalent quantity of ethyl magnesium bromide in the procedure of Example 14 results in 3α-hydroxy-2β-(7-chloro-3-ethyl-3-hydroxy-1-heptenyl)-5-oxocyclopentane-1α-heptanoic acid.

EXAMPLE 22

When an equivalent quantity of (5-bromopentanoyl-methylene)triphenyl phosphorane is substituted in the procedure of Example 8, there is produced 3α-tetrahydropyran-2-yloxy)-2β-(7-bromo-3-oxo-1-heptenyl)-5-oxocyclopentane-1α-heptanoic acid.

EXAMPLE 23

The substitution of an equivalent quantity of 3α-(tetrahydropyran-2-yloxy)-2β-(7-bromo-3-oxo-1-heptenyl)-5-oxocyclopentane-1α-heptanoic acid in the procedure of Example 9 results in 3αhydroxy-2β-(7-bromo-3-oxo-1-heptenyl)-5-oxocyclopentane-1α-heptanoic acid.

EXAMPLE 24

When an equivalent quantity of 3α-hydroxy-2β-(7-bromo-3-oxo-1-heptenyl)-5-oxocyclopentane-1αheptanoic acid is substituted in the procedure of Example 10, there is produced 3α-hydroxy-2β-(7-bromo-3-hydroxy-1-heptenyl)-5-oxocyclopentane-1α-heptanoic acid.

EXAMPLE 25

The substitution of an equivalent quantity of 3αhydroxy-2β(7-bromo-3hydroxy-1-heptenyl)-5-oxocyclopentane-1αheptanoic acid in the procedure of Example 11 results in 3α,5α-dihydroxy-2β-(7-bromo-3-hydroxy-1-heptenyl)cyclopentane-1α-heptanoic acid. This product is represented by the structural formula

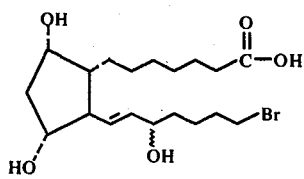

EXAMPLE 26

When an equivalent quantity of 3α-(tetrahydropyran-2-yloxy)-2β-(7-bromo-3-oxo-1-heptenyl)-5-oxocyclopentane-1α-heptanoic acid is substituted in the procedure of Example 14, there is produced 3α-hydroxy-2β-(7-bromo-3-hydroxy-3-methyl-1-heptenyl)-5-oxocyclopentane-1α-heptanoic acid.

EXAMPLE 27

When an equivalent quantity of 6-chlorohexanoyl chloride is subjected to the successive processes described in Examples 1 and 4, there is obtained [2-oxepanylidene)methyl]triphenylphosphonium chloride represented by the following structural formula

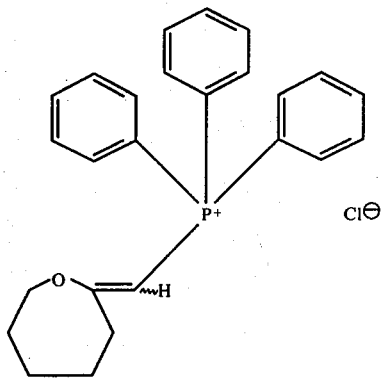

Substitution of an equivalent quantity of [(2-oxepanylidene)methyl]triphenylphosphonium chloride in the procedure of Example 6 results in [(2-oxepanylidene) -methyl]triphenylphosphonium bromide represented by the following structural formula

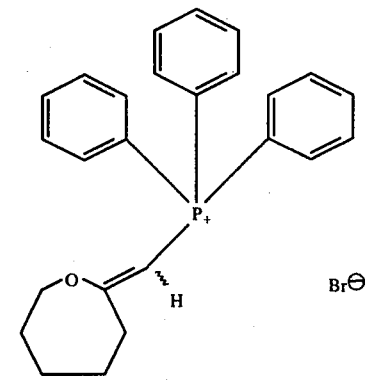

and melting at about 223°–226° C.

EXAMPLE 28

A solution of 59 parts of [(2-oxepanylidene)-methyl]triphenylphosphonium bromide in 200 parts by volume of 30% hydrobromic acid is heated at reflux temperature for about 18 hours, then is stripped of solvent under reduced pressure to afford the crude product as an oil. This oil was dissolved in water and benzene, and the pH adjusted to about 10 with aqueous sodium carbonate. The benzene layer is separated, washed twice with water and dried over anhydrous sodium sulfate. The desired product, (6-bromohexanoylmethylene)triphenylphosphorane in benzene is used immediately.

EXAMPLE 29

To a solution of 25 parts of 3α-[(dimethyl-t-butylsilyl)oxy]-2β-formyl-5-oxocyclopentane-1α-heptanoic acid in 500 parts by volume of dry benzene is added approximately one-half of the (6-bromohexanoylmethylene)-triphenylphosphorane of Example 28 under a nitrogen atmosphere. The solution is stirred for 8 hours at room temperature, at the end of which time the remaining (6-bromohexanoylmethylene)triphenylphosphorane of Example 28 is added. Stirring of this mixture is continued for approximately 36 hours longer, at the end of which time 90% of the solvent is removed by distillation under reduced pressure, thus affording the crude product as a red oil. This oil is purified by adsorption on 300 parts of silicic acid, followed by elution with 100% benzene to give 3α-[(dimethyl-t-butylsilyl)oxy]-2β-(8-bromo-3-oxo-1-octenyl)-5-oxocyclopentane-1α-heptanoic acid. Recovery of unreacted (6-bromohexanoylmethylene)triphenylphosphorane is effected by elution of the column with a 50:50 mixture of ethyl acetate-ethanol.

EXAMPLE 30

The substitution of an equivalent quantity of 3α-[(dimethyl-t-butylsilyl)oxy]-2β-(8-bromo-3-oxo-1-octenyl)-5-oxocyclopentane-1α-heptanoic acid in the procedure of Example 13 results in 3α,5α-dihydroxy-2β-(8-bromo-3α-hydroxy-1-octenyl)cyclopentane-1α-heptanoic acid. This product is characterized by 100-MHz nuclear magnetic resonance peaks in CD₃OD (deuterated methanol) at 230 cps (broad triplet), 343 cps (triplet), 410 cps (multiplet) and a complex pattern centered at 556 cps, and represented by the following structural formula

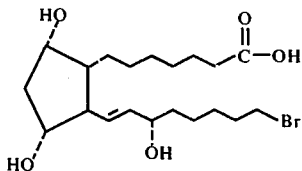

EXAMPLE 31

When an equivalent quantity of 3α-[(dimethyl-t-butylsilyl)oxy]-2β-(8-bromo-3-oxo-1-octenyl)-5-oxocyclopentane-1α-heptanoic acid is substituted in the procedure of Example 14, and the resulting product chromatographed on silica gel there is successively obtained 3α-hydroxy-2β-(8-bromo-3α-hydroxy-3β-methyl-1-octenyl)-5-oxocyclopentane-1β-heptanoic acid; characterized by 100-MHz nuclear magnetic resonance spectra peaks in CD₃OD at 230 cps (triplet), 345 cps (triplet), 525 cps (quartet) and 575 cps (doublet); 3α-hydroxy-2β-(8-bromo-3β-hydroxy-3α-methyl-1-octenyl)-5-oxocyclopentane-1α-heptanoic acid characterized by 100-MHz nuclear magnetic resonance spectra peaks in CD₃OD at 345 cps (triplet), 410 cps (multiplet), and 564 cps (multiplet); and 3α-hydroxy-2β-(8-bromo-3α-hydroxy-3βmethyl-1-octenyl)-5-oxocyclopentane-1α-heptanoic acid characterized by 100-MHz nuclear magnetic resonance spectra peaks in CD₃OD at 346 cps (triplet), 412 cps (multiplet) and 563 cps (multiplet).

The latter product is represented by the following structural formula

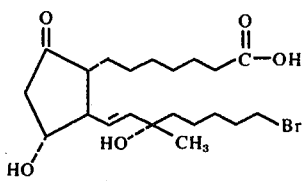

EXAMPLE 32

Substitution of an equivalent quantity of 3α-hydroxy-2β-(8-bromo-3α-hydroxy-3β-methyl-1-octenyl)-5-oxocyclopentane-1α-heptanoic acid in the procedure of Example 13 results in 3α,5α-dihydroxy-2β-(8-bromo-3α-hydroxy-3β-methyl-1-octenyl)cyclopentane-1α-heptanoic acid. This product is represented by the following structural formula

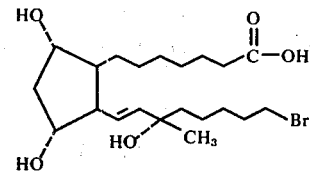

EXAMPLE 33

When an equivalent amount of 5-chloropentanoyl chloride is subjected to the successive processes described in the Examples 1,2,3 and 4, there is obtained [tetrahydro-2H-furan-2-ylidene)methyl]triphenylphosphonium chloride, melting at about 231°–234° C. This compound is represented by the following structural formula

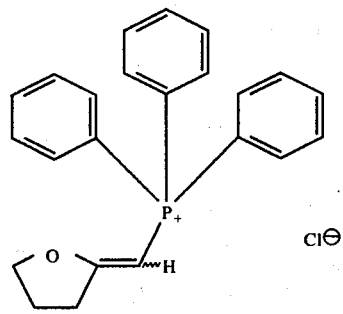

EXAMPLE 34

When an equivalent quantity of [(tetrahydro-2H-furan-2-ylidene)methyl]triphenylphosphonium chloride is subjected to the successive processes described in Examples 6,28,29 and 30, there is obtained 3α,5α-dihydroxy-2β-(6-bromo-3α-hydroxy-1-hexenyl)cyclopentane-1α-heptanoic acid. This product is represented by the structural formula

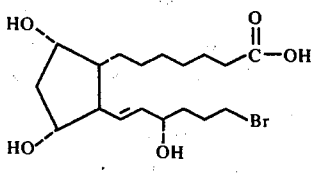

EXAMPLE 35

A mixture containing 1 part of 3α,5α-dihydroxy-2β-(7-chloro-3-hydroxy-1-heptenyl)cyclopentane-1α-heptanoic acid, 0.5 part of diazomethane and 20 parts of ether is kept at room temperature for about 5 minutes, at the end of which time acetic acid is added in order to destroy the excess reagent. The resulting mixture is then washed with aqueous sodium bicarbonate, dried over anhydrous sodium sulfate and stripped of solvent by distillation under reduced pressure to afford methyl 3α,5α-dihydroxy-2β-(7-chloro-3-hydroxy-1-heptenyl)-5-oxocyclopentane-1α-heptanoate.

EXAMPLE 36

A mixture consisting of 25 parts of 3α-hydroxy-2β-(7-chloro-3α-hydroxy-1-heptenyl)-5-oxocyclopentane-1α-heptanoic acid, 10 parts of acetic anhydride and 10 parts of pyridine is allowed to stand at room temperature for about 16 hours, then is poured carefully into cold excess aqueous citric acid. The resulting aqueous mixture is allowed to stand at room temperature for about 1 hour, then is extracted several times with ether. The combined ether extracts are washed with cold water, dried over anhydrous sodium sulfate and concentrated to dryness under reduced pressure. The resulting residue is purified by adsorption on a silicic acid chromatographic column, followed by elution with ethyl acetate in benzene, thus affording 3α-acetoxy-2β-(7-chloro-3α-acetoxy-1-heptenyl)-5-oxocyclopentane-1α-heptanoic acid.

What is claimed is:

1. A compound of the formula

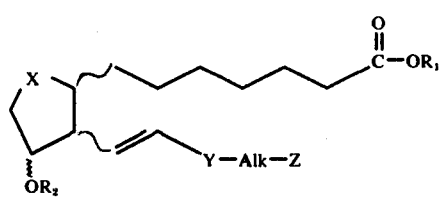

wherein $R_1$ is hydrogen or an alkyl radical containing 1–12 carbon atoms; $R_2$ is hydrogen, a tetrahydropyran-2-yl or trialkylsilyl radical, or alkanoyl radical containing 1–12 carbon atoms; X is a hydroxymethylene radical; Y is a radical of the formula

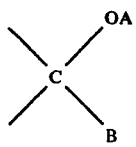

A being hydrogen or an alkanoyl radical containing 1–12 carbon atoms and B being hydrogen or an alkyl radical containing 1–12 carbon atoms; Z is a chloro, bromo, or iodo radical; Alk is an alkylene radical containing 3–8 carbon atoms; and the wavy lines represent the alternative α and β sterochemical configurations.

2. A compound according to claim 1 of the formula

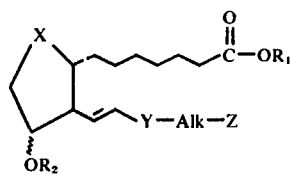

wherein $R_1$ is hydrogen or an alkyl radical containing 1–6 carbon atoms; $R_2$ is hydrogen, a tetrahydropyran-2-yl or trialkylsilyl radical, or alkanoyl radical containing 1–6 carbon atoms; X is a hydroxymethylene radical; Y is a radical of the formula

A being hydrogen or an alkanoyl radical containing 1–6 carbon atoms and B being hydrogen or an alkyl radical containing 1–6 carbon atoms; Z is a chloro or bromo radical; Alk is an alkylene radical containing 4–5 carbon atoms; and the wavy line represents the alternative α and β sterochemical configurations.

3. A compound according to claim 1 of the formula

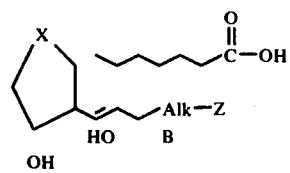

wherein X is a hydroxymethylene radical; B is hydrogen or an alkyl radical containing 1–6 carbon atoms; Z is a chloro or bromo radical; Alk is an alkylene radical containing 4–5 carbon atoms; and the wavy line represents the alternative α and β stereochemical configurations.

4. As in claim 1, the compound which is 3α,5α-dihydroxy-2β-(7-chloro-3α-hydroxy-1-heptenyl)cyclopentane-1α-heptanoic acid.

5. As in claim 1, the compound which is 3α,5α-dihydroxy-2β-(7-chloro-3β-hydroxy-1-heptenyl)cyclopentane-1α-heptanoic acid.

6. As in claim 1, the compound which is 3α,5α-dihydroxy-2β-(7-chloro-5-methyl-3-hydroxy-1-heptenyl)-cyclopentane-1α-heptanoic acid.

7. As in claim 1, the compound which is methyl 3α,5α-dihydroxy-2β-(7-chloro-3α-hydroxy-1-heptenyl)-cyclopentane-1α- heptanoate.

8. As in claim 1, the compound which is 3α,5α-dihydroxy-2β-(8-bromo-3α-hydroxy-1-octenyl)cyclopentane-1α-heptanoic acid.

9. As in claim 1, the compound which is 3α,5α-dihydroxy-2β-(8-bromo-3α-hydroxy-3β-methyl-1-octenyl)-cyclopentane-1α-heptanoic acid.

10. As in claim 1, the compound which is 3α,5β-dihydroxy-2β-(7-chloro-3α-hydroxy-1-heptenyl)cyclopentane-1α-heptanoic acid.

* * * * *